(12) United States Patent     (10) Patent No.:   US 9,005,131 B2
Tsukashima et al.     (45) Date of Patent:   *Apr. 14, 2015

(54) RESPIRATORY MONITORING, DIAGNOSTIC AND THERAPEUTIC SYSTEM

(76) Inventors: Ross Tsukashima, San Diego, CA (US); Jeffery D. Schipper, Ramona, CA (US); Leo R. Roucher, Jr., Rancho Santa Fe, CA (US); Erich H. Wolf, Vista, CA (US); Charles S. Bankert, Oceanside, CA (US)

( * ) Notice: Subject to any disclaimer, the term of this patent is extended or adjusted under 35 U.S.C. 154(b) by 2071 days.

This patent is subject to a terminal disclaimer.

(21) Appl. No.: 11/545,182

(22) Filed: Oct. 10, 2006

(65) Prior Publication Data

US 2007/0068810 A1    Mar. 29, 2007

Related U.S. Application Data

(63) Continuation-in-part of application No. 10/693,115, filed on Oct. 24, 2003, now Pat. No. 7,297,120, and a continuation-in-part of application No. 10/725,920, filed on Dec. 1, 2003, now Pat. No. 7,166,201, and a continuation-in-part of application No. 10/823,941, filed on Apr. 14, 2004, now Pat. No. 7,238,267.

(51) Int. Cl.
| | |
|---|---|
| *A61B 5/08* | (2006.01) |
| *A61B 5/083* | (2006.01) |
| *A61B 5/145* | (2006.01) |
| *A61B 5/00* | (2006.01) |
| *G01N 33/497* | (2006.01) |

(52) U.S. Cl.
CPC . *A61B 5/083* (2013.01); *A61B 5/08* (2013.01); *A61B 5/14539* (2013.01); *A61B 5/682* (2013.01); *G01N 33/497* (2013.01)

(58) Field of Classification Search
CPC .......... A61B 5/08; A61B 5/082; A61B 5/682; G01N 33/497

USPC ............................ 600/532, 543; 204/433, 435
See application file for complete search history.

(56) References Cited

U.S. PATENT DOCUMENTS

| | | | | |
|---|---|---|---|---|
| 5,479,815 A | * | 1/1996 | White et al. ................... | 73/23.3 |
| 7,101,340 B1 | * | 9/2006 | Braun ........................... | 600/532 |

(Continued)

*Primary Examiner* — Patricia Mallari
*Assistant Examiner* — Christian Jang
(74) *Attorney, Agent, or Firm* — Michael Edward Klicpera

(57) ABSTRACT

Disclosed is a system and method for monitoring the breath chemistry of a patient's breath using a specially designed self-condensing sensor module mounted in a mask, nasal cannula, headband with boom apparatus, or similar device for directing the patients' breath towards the self-condensing sensor. Monitoring of a patient's breath pH provided by the miniaturized self-condensing pH sensor provides for real-time monitoring of patient airway pH values. The specially designed self-condensing sensor module incorporates a data transfer means, e.g. direct wiring or by providing a transmitter with an antenna for wireless transferring of the pH data to a processing receiver. The self-condensing pH sensor comprises a multi-tubular design with the outer tubular member housing a silver chloride reference element, an ion conducting path, and an antimony sensor plug isolated in an inner tubular member that is co-linearly or coaxially configured with the outer tubular member. A transmitter with an antenna transfers the observed pH data by employing one of many wireless methods, such as radio-frequency (RF) energy. Alternately, the transfer of observed pH data is accomplished by direct wire methods. The pH data is transferred or updated at specific intervals, which can be varied according to the patient's needs, to the processing receiver that is engaged to the treatment apparatus. In the therapeutic configuration, the processing receiver computes and diagnoses the breath chemistry data and determines at what frequency the treatment apparatus should be activated.

67 Claims, 9 Drawing Sheets

(56) References Cited

U.S. PATENT DOCUMENTS

| | | | |
|---|---|---|---|
| 7,238,267 B2 * | 7/2007 | Wolf et al. | 204/433 |
| 7,297,120 B2 * | 11/2007 | Tsukashima et al. | 600/532 |
| 2003/0208133 A1 * | 11/2003 | Mault | 600/532 |
| 2004/0236244 A1 * | 11/2004 | Allen et al. | 600/532 |

* cited by examiner

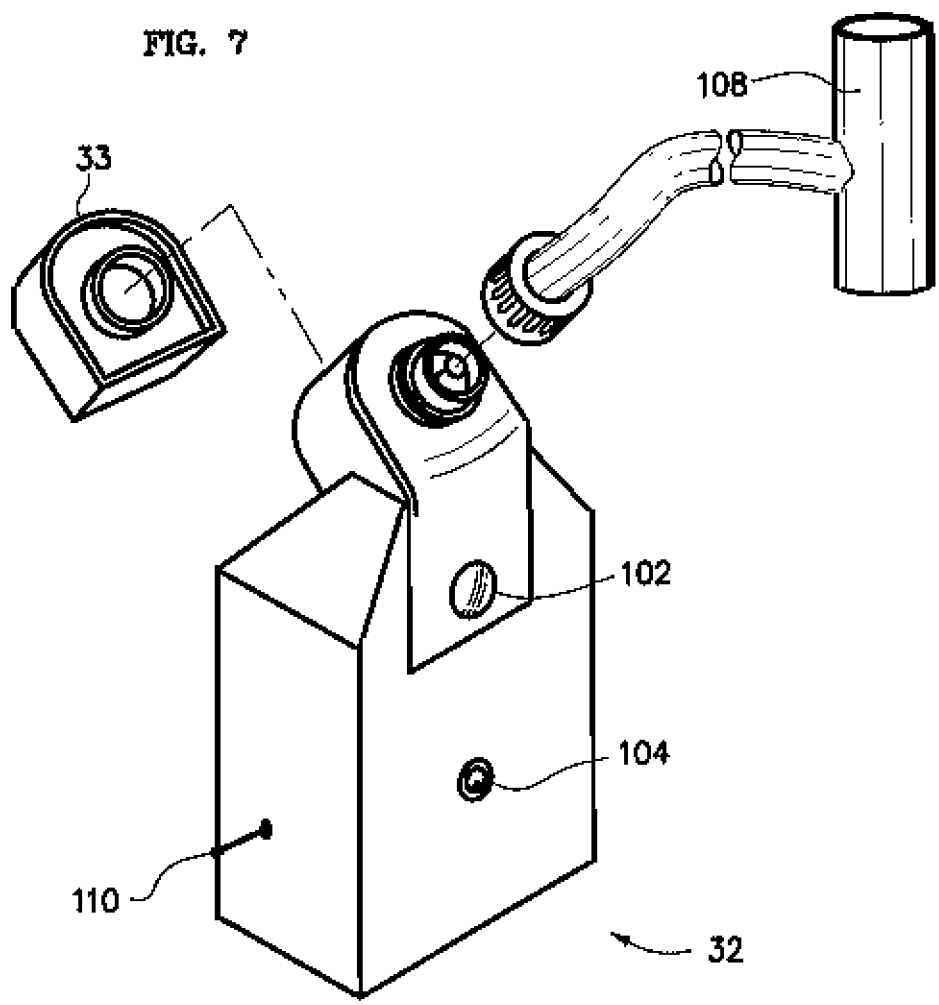

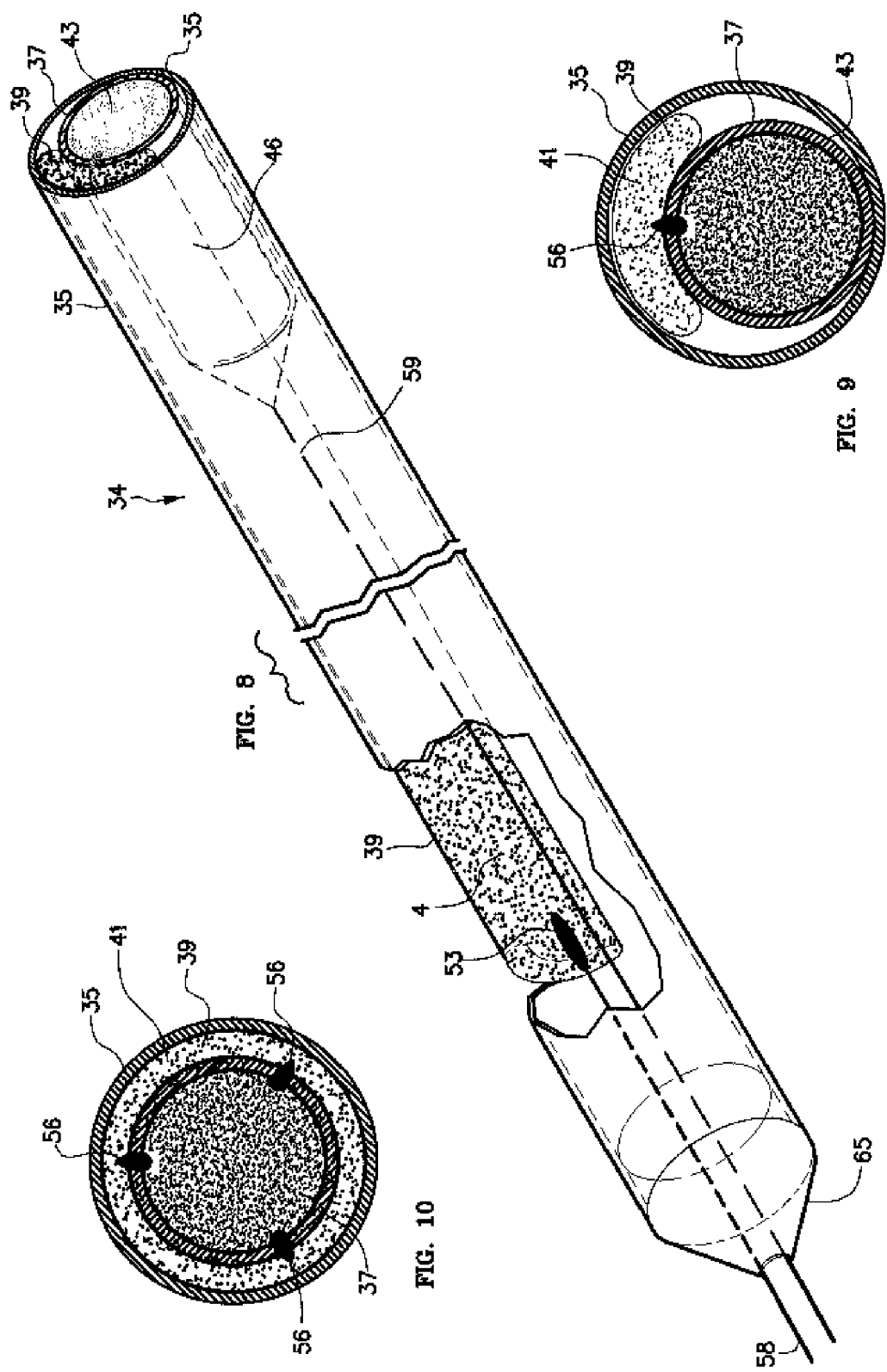

RESPIRATORY MONITORING, DIAGNOSTIC AND THERAPEUTIC SYSTEM

CROSS-REFERENCES

The present application is a continuation-in-part of patent application Ser. No. 10/693,115 filed on Oct. 24, 2003 now U.S. Pat. No. 7,297,120 entitled "A Respiratory Monitoring, Diagnostic and Therapeutic System" currently and a continuation-in-part of patent application Ser. No. 10/725,920 filed on Dec. 1, 2003 now U.S. Pat. No. 7,166,201 and patent application Ser. No. 10/823,941 filed on Apr. 14, 2004 now U.S. Pat. No. 7,238,267 both entitled "A Self-Condensing pH Sensor". These applications are incorporated herein by this reference.

FIELD OF THE INVENTION

The field of art to which this invention relates is in the monitoring of certain parameters and transfer of such information to facilitate the diagnosis or therapeutic treatment for patients suffering from respiratory diseases, such as asthma, laryngopharyngeal reflux disease (LPRD), chronic obstructive pulmonary disease (COPD), and obstructive sleep apnea (OSA). More specifically, the present invention monitors the pH level of a patient's breath and provides data for diagnosis or for determining the frequency and volume of a therapeutic dose to be administered to the patients' airways. Furthermore, it details the integration of known pH sensor materials to achieve a novel and compact pH sensor probe. Because of the proximity and orientation of the sensor's elements, it is able to self-condense and monitor pH changes of humidified gases as well as liquids.

BACKGROUND OF THE INVENTION

Recently, it has been reported that the monitoring of acidity or pH of a patient's breath could help physicians in estimating the degree of air passage inflammation, now considered a key contributor to asthma, LPR and other respiratory conditions. Asthma is characterized by symptoms of wheezing, coughing, chest tightness, and shortness of breath. Manifestations include constriction (the tightening of the muscles around the airways) and inflammation (the swelling and irritation of the airways) that can be triggered through exposure to smoking, dust mites, pets, activity, cold, infection, weather, pollen, etc.

A clinical study of people with chronic obstructive pulmonary disease (COPD), bronchiectasis and asthma demonstrated more acidic levels in COPD and bronchiectasis patients, which is indicative of the chronic inflammation that these patients experience. This study also observed an increased acidic level measured from the breath of patients suffering from moderate asthma when compared to mild forms of the disease. It was also found that the asthmatic's breath was much more acidic during asthma attacks, but normalized after anti-inflammatory medication was administered.

This data suggests that the monitoring of an asthmatic's breath for pH might be an effective way to measure the degree of inflammation in the air passages. Furthermore, this data suggests that close monitoring of an asthmatic's breath pH could lead to prompt and effective treatment, minimizing the occurrence of asthma attacks and providing overall better asthma management.

It is estimated that 18-26 million people in the United States suffer from asthmatic conditions ranking this disease as the $8^{th}$ worst chronic condition in the US. It is also believed that over 5.6 million of these asthma sufferers are under the age of 18.

Studies have also shown that gastro-esophageal reflux (GER) affects approximately 40% of the US adult population and that 60-80 percent of all asthma patients have GER. Gastro-esophageal reflux is a condition in which gastric acid refluxes from the stomach into the esophagus. Frequent reflux episodes may result in a potentially severe problem known as gastro-esophageal reflux disease (GERD). GER is the most common cause of dyspepsia or heartburn. GER can also manifest in the micro-aspiration of acid from the esophagus into the airway and lungs, damaging tissue, and causing irritation of the vagus nerve. This irritation of the vagus nerve, which is common to both the esophagus and the bronchial tree, can cause constriction of the airway. Acid reflux above the lower esophageal sphincter can cause anatomical damage and is linked to sleep disordered breathing. It has also been found that bronchial dilator drugs can relax the lower esophageal sphincter and trigger GERD induced asthmatic conditions. Sleep apnea has also been found to trigger reflux events. Testing for GER and the diagnosis of GERD are typically accomplished by measuring pH with catheter based devices.

These current pH monitoring methods suffer from the following drawbacks: 1) the current method requires an invasive procedure to place a pH measurement catheter or implanted pH measurement capsule in the patient's esophagus, 2) the procedure is not well tolerated by some patients, 3) the catheter or capsule placement must be performed by a physician, 4) the capsule cannot be placed above the Upper Esophageal Sphincter (UES) to measure airway pH, and 5) there are no defined standards for evaluation of pH above the UES.

Accordingly, there is a need in this art for a novel, pH diagnostic and monitoring system with electronic or wireless communication linked to a processing receiver that can also be used to activate a therapeutic nebulizer/atomizer/humidifier for treating asthmatic or other respiratory conditions.

SUMMARY OF THE INVENTION

The present invention pertains to an invention for monitoring the breath chemistry of a patient's breath using a specially designed self-condensing sensor module mounted in a mask, nasal cannula, headband with boom apparatus, or similar device for directing the patients' breath towards the self-condensing sensor. The system provides a means for communicating this data in real-time to a processing receiver for monitoring, diagnosing, or treating disease abnormalities in the patient. The system interprets the data and has a means for determining the frequency and volume of a therapeutic dose to be administered to a patient, typically with a respiratory condition such as asthma. Monitoring of a patient's breath pH is provided by the system that includes a miniaturized self-condensing pH sensor, providing for real-time monitoring of patient airway pH values.

The specially designed self-condensing sensor module incorporates a data transfer means, e.g. direct wiring or by providing a transmitter with an antenna for wireless transferring of the pH data to a processing receiver.

The self-condensing pH sensor comprises a multi-tubular design with the outer tubular member housing a silver chloride reference element, an ion conducting path, and an antimony sensor plug isolated in an inner tubular member that is co-linearly or coaxially configured with the outer tubular member.

A transmitter with an antenna transfers the observed pH data by employing one of many wireless methods, such as radio-frequency (RF) energy. Alternately, the transfer of observed pH data is accomplished by direct wire methods.

The pH data is transferred or updated at specific intervals, which can be varied according to the patient's needs, to the processing receiver that is engaged to the treatment apparatus. In the therapeutic configuration, the processing receiver computes and diagnoses the breath chemistry data and determines at what frequency the treatment apparatus should be activated.

The present invention mask and self-condensing pH sensor module may also be fitted with a means to remove the condensed liquid through an exhaust port or a connected pneumatic hose to remove unnecessary and accumulated breath condensate.

These and other features, aspects and advantages of the present invention will become better understood with reference to the following descriptions and claims.

BRIEF DESCRIPTION OF THE DRAWINGS

FIG. 7 is a schematic representation of the treatment nebulizer/atomizer/humidifier device, demonstrating a base unit having an on/off switch, operating lights, a medicament storage container, and interconnection for attaching the pneumatic hose.

FIG. 8 is a partially sectional side view of the sensor apparatus demonstrating in detail the orientation and components of the pH sensing means.

FIG. 9 is a top view of the terminal end of the sensor apparatus demonstrating the offset co-linear position of the antimony sensor and the reference wick with a condensed droplet electrically bridging the antimony sensor and the reference wick.

FIG. 10 is a top view of the terminal end of another embodiment sensor apparatus demonstrating the position of the reference wick surrounding an inner coaxially positioned tubular member containing the antimony sensor with several condensed droplets electrically bridging the antimony sensor and the reference wick.

DESCRIPTION OF THE PREFERRED EMBODIMENTS

The present invention provides a system and method for monitoring physiological parameters from a patient's exhaled breath and communicates this information to a processing computer/receiver that diagnoses, stores, or displays the information. The system can use computational instructions to activate and de-activate an electrically connected treatment nebulizer/atomizer/humidifier device, and can be integrated with a continuous positive airway pressure (CPAP) device.

Figure 1:
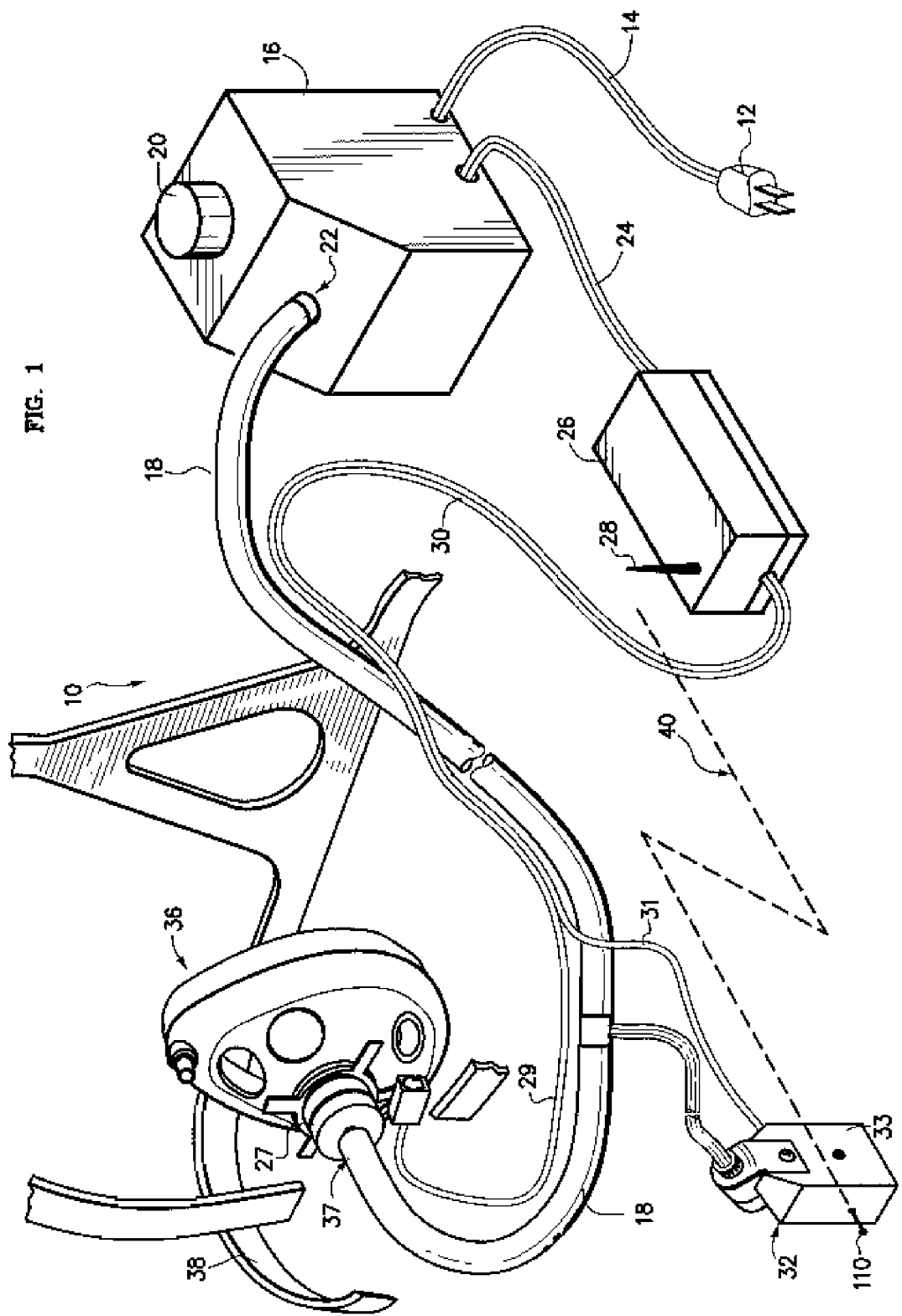
FIG. 1 is a perspective representation of the present invention systems, showing the various components of the system, including a mask apparatus fitted with a pH sensing eans, an optional continuous positive airway pressure (CPAP) device connected to the mask type apparatus, a processing receiver electrically connected to said mask apparatus, and a nebulizer/atomizer/humidifier device electrically connected to the processing receiver.

FIG. 1 illustrates that the present invention consisting of a system 10 comprised of several components. As shown in the Figure, a typical mask apparatus 36 is fitted with a securing strap or typical headgear apparatus 38. The mask configuration is only one embodiment contemplated by the Applicants. The present invention can perform in a mask-less configuration, with other embodiments consisting of mounting the sensor assembly to a headband or pair of goggles that suspends the sensor assembly within the patient's breathing airway. If the example mask apparatus 36 is employed, it is generally fabricated from a polymeric and/or silicone material and configured to fit over a patient's nose, or nose and mouth, to assist in breathing conditions. The securing strap 38 is made from a flexible material and is positioned around the patient's head such that the mask substantially engages the patient's face and mouth area, minimizing ambient air from entering the boundaries of the mask. It is contemplated by the Applicants that other mask configurations, including a sensor module without mask, or mask-less configurations, and different positions of the components of the present invention, can still achieve the goal of monitoring, diagnosing and treating respiratory and medical conditions in patients.

Shown attached to the front of the mask apparatus 36 is a housing 27 that contains the components necessary for condensing the patient's breath and monitoring certain chemical parameters. The housing 27 can be machined or molded from a variety of polymeric materials including polyethylene, polypropylene, polyvinyl chloride, polystyrene, ABS, nylon, delrin, or polyethylene terephthalate (PET), or from metallic materials, such as aluminum or other biocompatible metallic alloys.

The mask apparatus 36 may be connected to the exit port 22 of a CPAP device 16 by means of a pneumatic hose 18. The hose can be manufactured from a variety of materials, including polymers such as polyethylene, polypropylene, polyvinyl chloride or silicone. The material used for the hose should be resistant to water and acidic environments and should not interfere or interact with any medicaments employed in the present invention. CPAP air exits port 22 and travels along the length of the pneumatic hose 18 to the internal sampling cavity created by the general mask apparatus covering the patient's face. The CPAP device has a control means 20 for increasing and decreasing the volume of air generated by the apparatus and the output of an optional humidification device. The CPAP device and humidifier are powered by an electrical source such as a standard plug 12 and cable 14.

Shown connected to the sensor body 27 is an electrical wire 29 that communicates the sensor 34 with a processing receiver 26. Also shown is a combined cable 30 having the electrical wire 29 from the sensor 34 and electrical means 31 connecting the therapeutic nebulizer 32 to the processing receiver 26.

Electrical wire 29 is typical in that the internal core comprises an electrically conductive metallic material and is encased by a nonconductive jacket. Processing receiver 26 is connected to the CPAP device 16 by an electrical wire 24 for controlling the activation of air generated by the CPAP device 16 and transferred to the typical mask apparatus 36. Also, an electrical connection by means of a wire 31 to the processing receiver 26 is a treatment nebulizer/atomizer/humidifier device 32. As an alternate method, a wireless means 40 can be utilized instead to communicate between the processing receiver 26 with an antenna 28 to the treatment nebulizer/atomizer/humidifier device 32. Although not shown in detail in FIG. 1, a wireless means also can be employed to communicate between the typical mask apparatus 36 and the processing receiver 26. In addition, a wireless means also can be employed to communicate between the processing receiver 26 and the CPAP device 16. As appreciated by those skilled in the art, wireless means for communicating between various components can be accomplished using radio frequency waves, microwaves, ultrasonic waves, or light optics.

The treatment nebulizer/atomizer/humidifier device 32 is pneumatically connected to hose 18 at some point along its length between the CPAP device 16 and the typical mask apparatus 36. The treatment nebulizer/atomizer/humidifier device 32 has a medicament storage chamber 33 where various types of therapeutic medicaments can be delivered to the pneumatic system and to the patient at intervals commanded by the processing receiver 26. If necessary, a scrubber can be added to the mask air outlet to remove excess medicament if it is inappropriate to vent the medicament into the room air.

Figure 2:
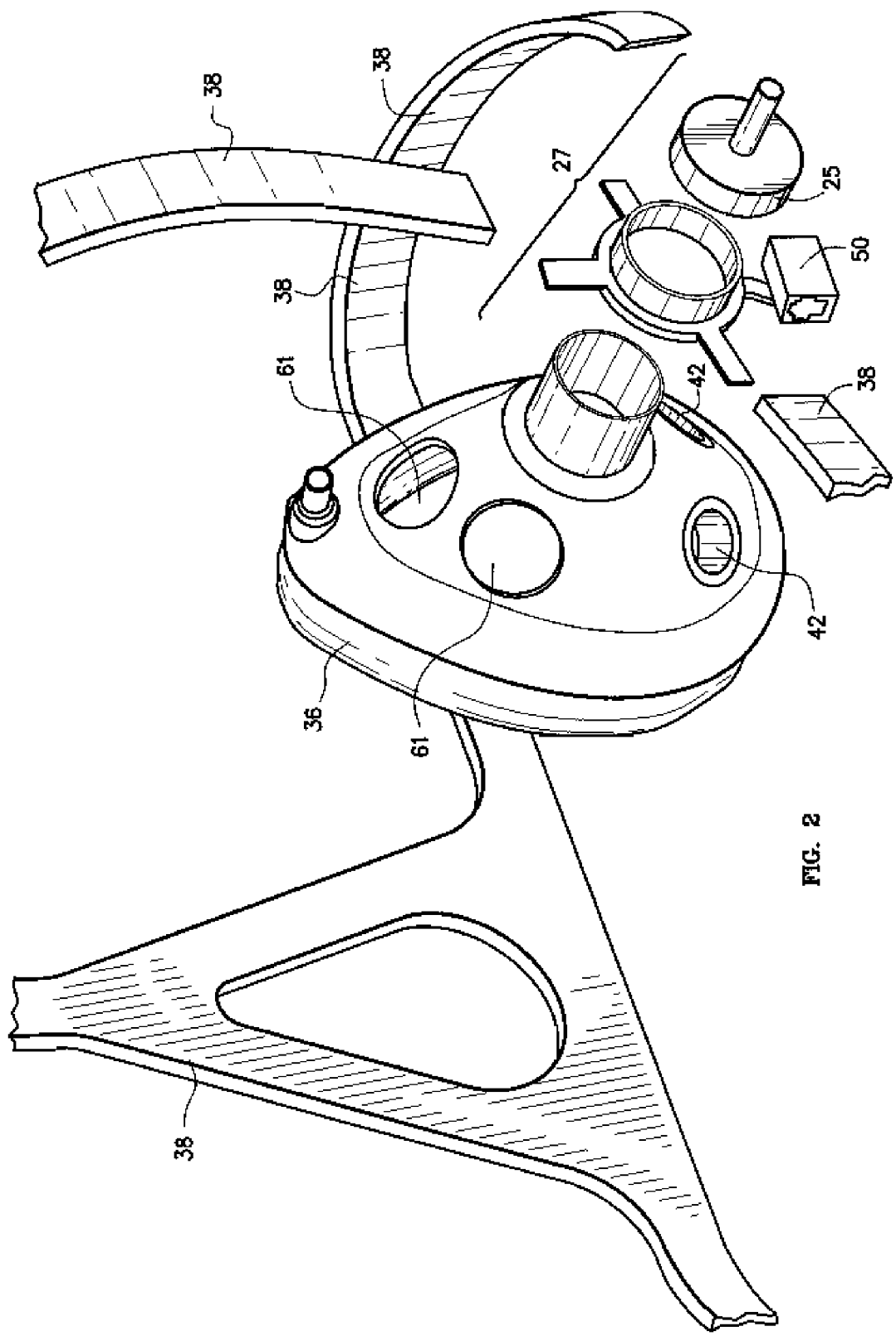
FIG. 2 is an exploded sectional representation view of the mask apparatus demonstrating in more detail of the orientation and components of the mask and the pH sensing holding mechanism.

FIG. 2 is an exploded sectional representation view of the mask apparatus 36 demonstrating in more detail of the orientation and components of the mask and the pH sensor holding mechanism. Shown in the Figure are the intake ports 42 and exhaust ports 61. The senor body 27 is composed of several parts including a sensor holding means 25 and an electrical communication means 50. Also shown is the strap 38 attached to the mask apparatus 36 at various points.

Figure 3:
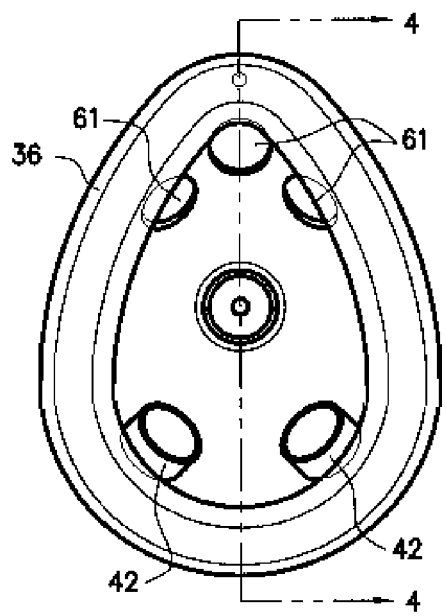
FIG. 3 is an inside view showing the configuration and general location of the mask air passageways.

FIG. 3 is an inside view showing the configuration and general location of the air passageways. Shown from an inside view are the intake ports 42 and exhaust ports 61.

Figure 4:
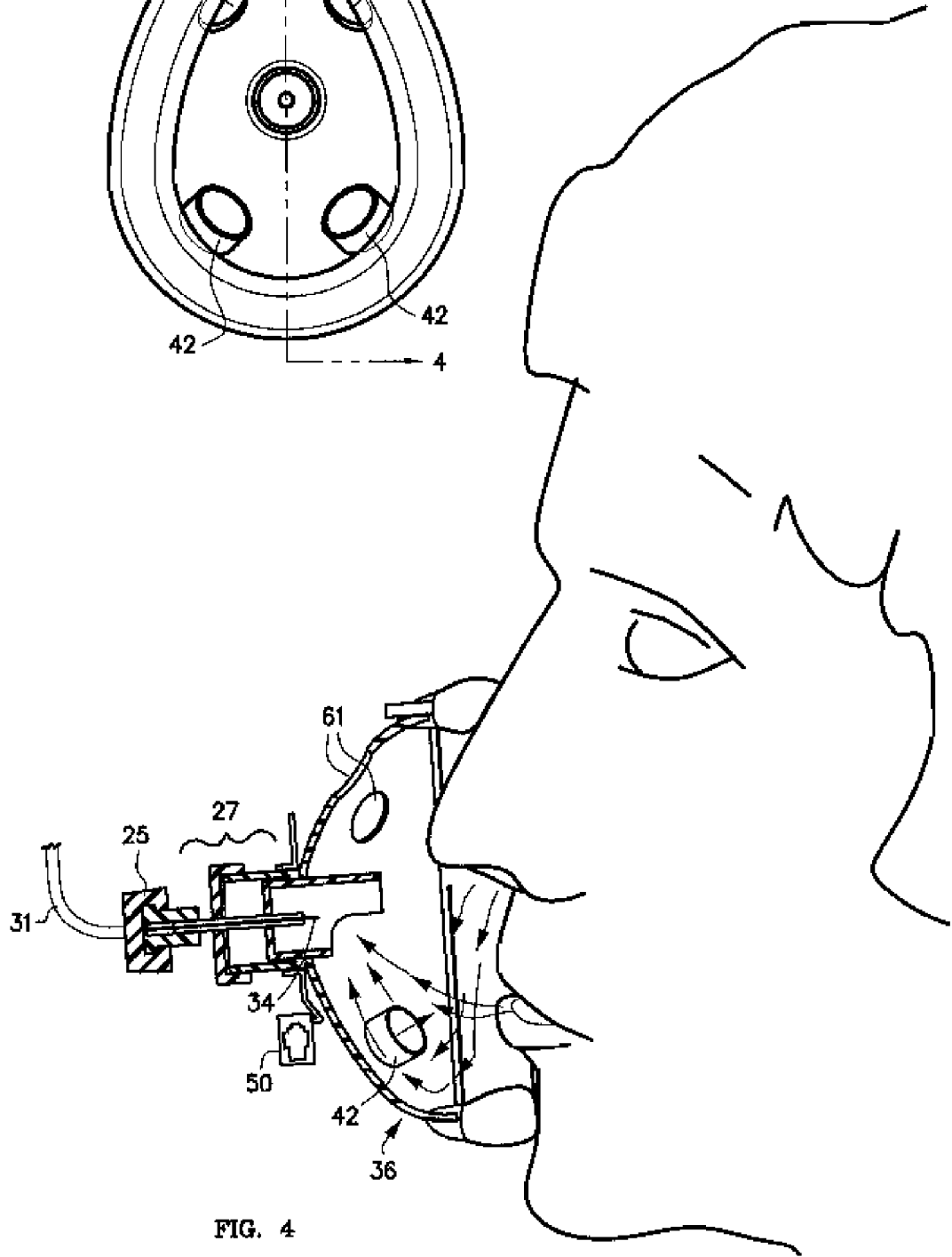
FIG. 4 is a sectional side view taken from FIG. 3 demonstrating in more detail the relative locations of the mask air passageways, self-condensing sensor holding mechanism, the self-condensing sensor, and the general flow of the patient's breath when used in clinical applications.

FIG. 4 is a sectional side view taken from FIG. 3 demonstrating in more detail the relative locations of the mask components, the self-condensing sensor holding mechanism 27, the self-condensing sensor 34, and the general flow of the patient's breath when used in clinical applications.

Figure 5:
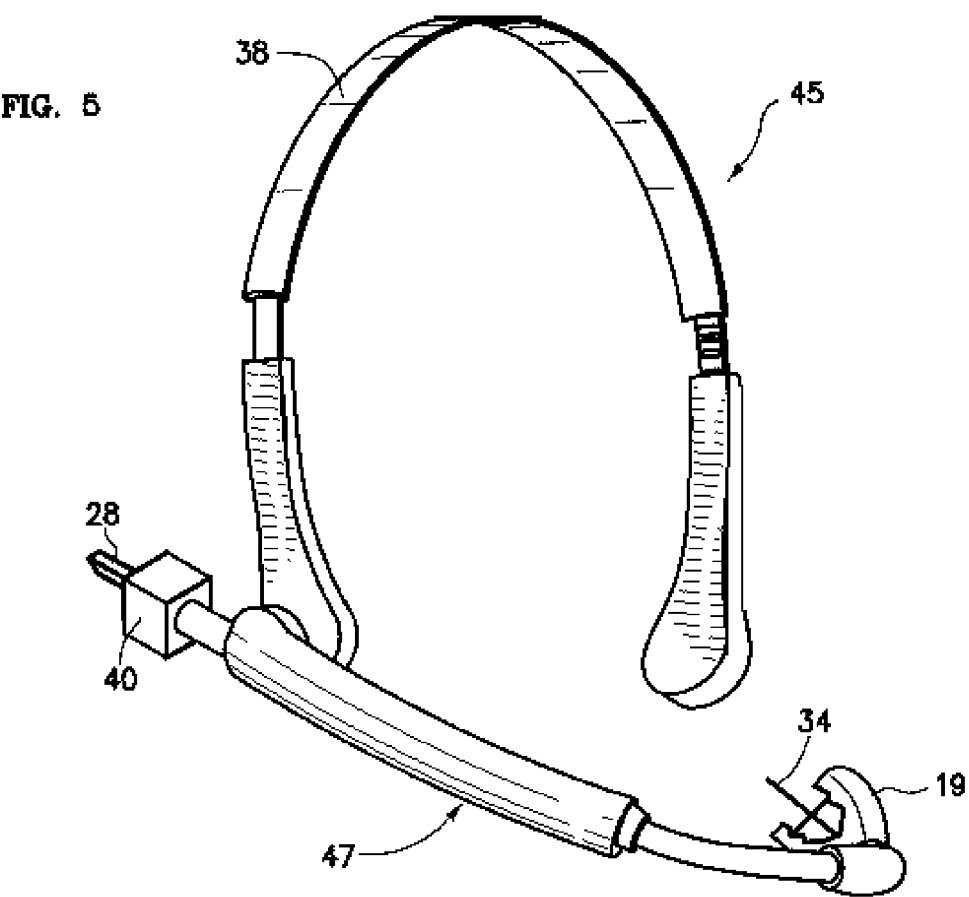
FIG. 5 is a perspective representation of another embodiment of the present invention systems, showing the various components of the system, including the pH self-condensing sensor means suspended from a mask-less headband apparatus with an extended boom to locate the self-condensing pH sensor within the patient's breath airway.

FIG. 5 is a perspective representation of another embodiment of the present invention systems, showing the various components of the system. The self-condensing pH senor 34 is shown incorporated within a shield 19 near the terminal end of an extended boom 47 attached to the mask-less headband apparatus 45. The extended boom 47 is positioned to locate the self-condensing pH sensor 34 within the patient's breath airway.

Figure 6:
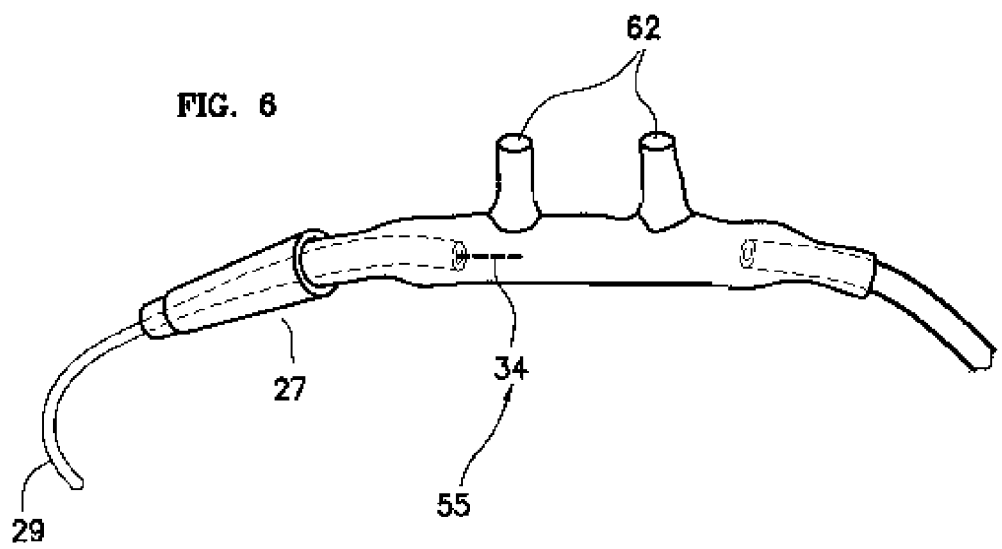
FIG. 6 is a perspective representation of another embodiment of the present invention systems, showing the various components of the system, including the pH self-condensing sensor means incorporated within a nasal cannula to locate the self-condensing pH sensor within the patient's breath airway.

Another example of a mask-less apparatus for containing the sensor is demonstrated in FIG. 6 where said mask-less apparatus comprises a nasal cannula 55. The self-condensing sensor 34 is secured with a housing 27 that attached to one end of the nasal cannula 55. The self-condensing pH sensor 34 is located in the nasal cannula 55 such that it is in pneumatic communication with the nose ports 62 of the nasal cannula 55 which are generally positioned within the nostrils of a patient.

In this example, as well as the embodiment shown in FIG. 5, the pH of the patient's breath can be continuously monitored. Extending from the self-condensing pH sensor 34 of FIG. 6 are the sensor electrical communication means 29 which is electrically connected to the display/processing means 26. Alternately, as shown in FIG. 5 a wireless means 40 with an antenna 28 are wirelessly communicating to display/processing means 26. The self-condensing sensor 34 can provide an immediate reading of the pH of the patient's breath or the self-condensing pH sensor 34 could be used to measure the pH of the patient's breath for a period of time to monitor and diagnose certain respiratory conditions. Another potential use of the self-condensing pH sensor 34 in clinical applications is to detect the absence of breath, a condition known as sleep apnea.

FIG. 7 is a schematic representation of the treatment nebulizer/atomizer/humidifier device 32, demonstrating a base unit having an on/off switch 102, operating lights 104, a medicament chamber 33, and interconnection 108 for attaching to the pneumatic hose 18. The treatment nebulizer/atomizer/humidifier device 32 has an outer shell surrounding various mechanical and electrical components that function to deliver the therapeutic dose. The shell can be made of a variety of materials, including plastics such as polyethylene, polystyrene, ABS, nylon, delrin, or polyethylene terephthalate (PET). The treatment nebulizer/atomizer/humidifier device 32 communicates with the processing receiver by direct wiring (not shown) or by use of wireless means employing an antenna means 110. The base unit and various components of the treatment nebulizer/atomizer/humidifier can be fabricated from polymeric or metallic materials. Operating light 104 can consist of LED, LCD, fluorescent, or halide or other means to communicate such conditions, as on/off, medicament chamber empty, etc. Also, the Applicant contemplates that a plurality of operating lights can be employed having different functions. The art associated with atomization of particles and humidification processes are known in the art. Many commercially available units can satisfy the basic requirements for the treatment nebulizer/atomizer/humidifier device 32. One such device is the MicroAir portable ultrasonic nebulizer manufactured by Omron Healthcare, Inc. of Vernon Hills, Ill. This device can be modified or fabricated so that 1) it can be remotely activated by the processing receiver 26, and 2) adapted to connect to the pneumatic tube by an appropriate connection 108 as shown in FIG. 7.

The medicament chamber 33 can contain liquid, gaseous or powdered therapeutics that the treatment nebulizer/atomizer/humidifier device 32 is designed to administer to the pneumatic system upon instructions from the processing receiver 26. It is contemplated that the medicament chamber 33 could include a plurality of medicaments in various compartments in the medicament chamber 33. It is also contemplated that a treatment nebulizer/atomizer/humidifier device 32 can be selected to administer one or more, or in a combination, multiple medicaments stored in the medicament chamber 33. Either a continuous method or, to conserve medicine, a pulsed method corresponding with each breath detected by conventional means can be employed by the present invention.

FIG. 8 illustrates the partially sectional side view of the self-condensing pH sensor 34. As shown in this Figure, the partially sectional side view of the sensor apparatus demonstrates various components and their orientation.

The self-condensing pH sensor 34 consists of an outer tubular member 35 that is usually fabricated by an extrusion or dip coating process using a variety of polymeric materials including polyimide, polyethylene, polypropylene, polyvinyl chloride, polystyrene, ABS, nylon, delrin, polyethylene terephthalate (PET), fluorinated ethylene-propylene (FEP) or polytetrafluoroethylene (PTFE). The outer tubular member 35 generally has an outside diameter in the range of 0.010" to 0.050", and preferably between 0.020" and 0.030". Its wall thickness is typical for its diameter and generally is in the range of 0.00025" to 0.002" and preferably between 0.0005" and 0.001". The outer tubular member may include a coating specific for certain applications, e.g. protection from acid environments, dielectric isolation, etc.

Co-linearly or coaxially aligned within the outer tubular member 35 is an inner tubular member 37 that is also usually fabricated by an extrusion or dip coating process using a variety of polymeric materials including polyimide, polyethylene, polypropylene, polyvinyl chloride, polystyrene, ABS, nylon, delrin, polyethylene terephthalate (PET), fluorinated ethylene-propylene (FEP) or polytetrafluoroethylene (PTFE). The inner tubular member 37 has an outside diameter smaller than the inside diameter of the outer tubular member 35 and generally is in the range of 0.015" to 0.030", and preferably between 0.020" and 0.028". Its wall thickness is typical for its diameter and generally is in the range of 0.00025" to 0.002" and preferably between 0.0005" and 0.001".

Located within the inner tubular member 37 is an antimony reference element 46 having a surface area 43 at the terminal end. The antimony element 46 is generally 99% pure and free from significant contaminates. The Applicant contends that the antimony sensor could be replaced with other metallic substances like antimony that exhibit a change in electrical potential when immersed in different pH fluids. Furthermore, other potential materials such as specially formulated polymers, semiconductor technology, Ion Sensitive Field Effect Transistors ("ISFET's"), optical sensing, capacitive sensing, and nanotechnology could be employed.

The antimony reference element 46 is engaged at its proximal end to an electronic communication means 59. Typically the electronic communication means 59 comprises electrical wire that has an internal core comprising an electrically conductive metallic material which is encased by a nonconductive jacket. The means of engagement typically employs standard soldering technology and can be supported by a variety of means to provide strain relief. The terminal surface 43 of the antimony reference element 46 defines the distal terminal boundary of the sensor and is the surface that is exposed to liquid or humid gaseous environments. As shown in FIG. 8, the antimony reference element 46 and the reference electrode 39 are substantially in the same plane. However, it is anticipated by the Applicants that several designs or embodiments in which the antimony element 46 and reference electrode 39 are not substantially in the same plane. For example, a coaxial design in which the antimony element 46, protruding beyond the center of the sensor terminal end, has the advantage of providing a greater surface area of antimony element 46 to react with the condensing sample. In addition, a co-linear sensor in which the antimony sensor protrudes past the plane of the wick 41 and the extension that is angled towards the wick 41 provides the advantage of providing a greater surface area but additionally diminishes or reduces the angle between the reference electrodes. Reducing the angle between the wick 41 and the antimony element 46 may provide a more accurate measurement in low humidity conditions. Still another design or embodiment entails either the coaxial or co-linear design, where the antimony element 46 is recessed from the plane of the wick 41. This design has the potential for greater stability due to the larger film thickness that condenses and resides on the antimony face. In addition, a further benefit of this design is the potential for greater sensitivity in sleep apnea clinical conditions due to the increased angle between the electrodes at the top of the recess. This increased angle may cause the surface tension to break contact between the electrodes more rapidly than on a planar design in the event of a decrease in fluid deposition.

The performance of the sensor may be enhanced in some environments by the inclusion of a coating on this distal surface. One example would be a hygroscopic coating to enhance the absorption and retention of moisture on the sensor in humidified gases and aerosols. Materials such as hydrophilic polyurethanes, polyacrylamides, poly(2-hydrox-ethylmethacrylate), other methacrylate copolymers, perfluorinated polymers, polysaccharides, polyvinylchloride polyvinyl alcohol and silicones could all be utilized as surface enhancements either alone, in combination, or with modifications.

Located proximally, from a range of 1-8 centimeters from the proximal end of the antimony element 46 and preferably 3-5 centimeters, is a reference element 53. Said reference element 53 is primarily composed of a silver core surrounded with a coating of silver chloride. Technology of dipping a silver core in a high temperature bath of silver chloride to produce the silver chloride coating is employed in the present invention. The resulting coating generally is 0.0001" to 0.010" in thickness, and preferably 0.001" to 0.005". Reference element 53 is engaged to an electrical communication means 58, e.g. typical wire that extends to the proximal end of the outer tubular member 35 and can terminate in a typical electrical connector (not shown). An adhesive or polymer plug 65 can be placed in a proximal position to the reference element 53 that is engaged to the outer tubular member 35 which provides support for electrical communication means 58 and 59 and provides proximal sealing of the outer tubular member 35.

A reference wick 41 is located between the inside surface of the outer tubular member 35 and the outer surface of the inner tubular member 37. In one embodiment (see FIG. 9), the inner tubular member 37 is coaxially offset with the outer tubular member 35. The reference wick 41 partially surrounds the inner tubular member 37 where the area of the offset coaxial design is large enough to contain the fabric or mesh configuration of the reference wick 41. As discussed in more detail below, reference wick 41 has a mesh or fibrous configuration which functions to entrain or retain an ion conducting fluid 39. As the mesh or fibrous configuration is compacted, less ion conduction fluid 39 can be entrained or retained. Reference wick 41 is physically separated from the antimony sensor 46 by the wall of the inner tubular member 37. It is important to the present invention that the reference wick 41 does not engage or contact the antimony sensor 46 at any point. The reference wick 41 can be fabricated from a variety of polymeric based materials. Examples of such materials are polysaccharides, (cotton, regenerated cellulose) polyester, polyethylene, polypropylene, polyvinyl chloride (PVC), polystyrene, ABS, nylon, delrin, polyethylene terephthalate (PET), polytetrafluoroethylene (PTFE), collagen, Hytrel (thermoplastic polyester elastomer), or any material or combination of materials which exhibit a weave, felt or mesh design that facilitates wicking or ion conduction. One example of a preferable material for the reference wick 41 is a polyester fabric mesh. The reference wick 41 functions as a plurality of capillary tubes which transport electrical ions between the antimony element face 43 and reference element 53.

The reference wick 41 is impregnated with an ion conduction fluid 39. Typical conduction fluids include those that contain sodium chloride or potassium chloride and water. One example that can be used with the sensor is a polysaccharide based gel that is incorporated with a 2-10 percent, with a preferred range of 3-5 percent, solution of potassium chloride and water. Other materials that can function as the reference wick 41 with an ion conduction fluid 39 include ion carrying gels, hydrogels, and excipients. These gels, hydrogels, and excipients aid in reducing the diffusion of contaminants into the ion conduction fluid 39.

FIG. 9 is a top view of the terminal end of the self-condensing pH sensor apparatus 34 demonstrating the offset coaxial position of the antimony element 46 and the reference wick 41 with a condensed droplet 56 electrically bridging the antimony element 46 and the reference wick 41. The self-condensing sensor 34 functions as an electric cell or battery where chemical energy is converted into electrical energy. The sensor utilizes the potential difference that exists between the sensor's different elements: the antimony sensor 46 and silver chloride reference 53. When a condensed droplet joins the antimony element terminal surface 43 with the reference wick 41, a voltage potential is created between the antimony sensor 46 and the reference element 53. This voltage potential changes relative to the reference element 53 depending on the pH of the condensate that the sensing elements are exposed to. Therefore, by monitoring the potential difference that exists between the antimony sensor 46 and the silver chloride reference 53, the pH of the condensed droplet can be accurately measured.

FIG. 10 is a top view of the terminal end of another embodiment sensor apparatus demonstrating the position of the reference wick 41 surrounding an inner coaxially positioned tubular member 37 that contains the antimony sensor 46. In this embodiment, there is no offset between the coaxially positioned tubular members and the inner tubular member 37. Inner tubular member 37 is centered within the outer tubular member 35 with reference wick 41 completely surrounding the inner tubular member 37. This embodiment has the advantage that any droplet which condenses along the circumference of the inner tubular member 37 can potentially form a bridge or junction between the antimony element 46 and the silver chloride reference 53. Several condensed droplets 56 are shown in FIG. 10 to electrically bridge between the antimony element 46 and the reference wick 41. In this particular situation, the average pH of all three droplets would be represented in the potential difference and measured by the sensor apparatus 34.

Figure 11:
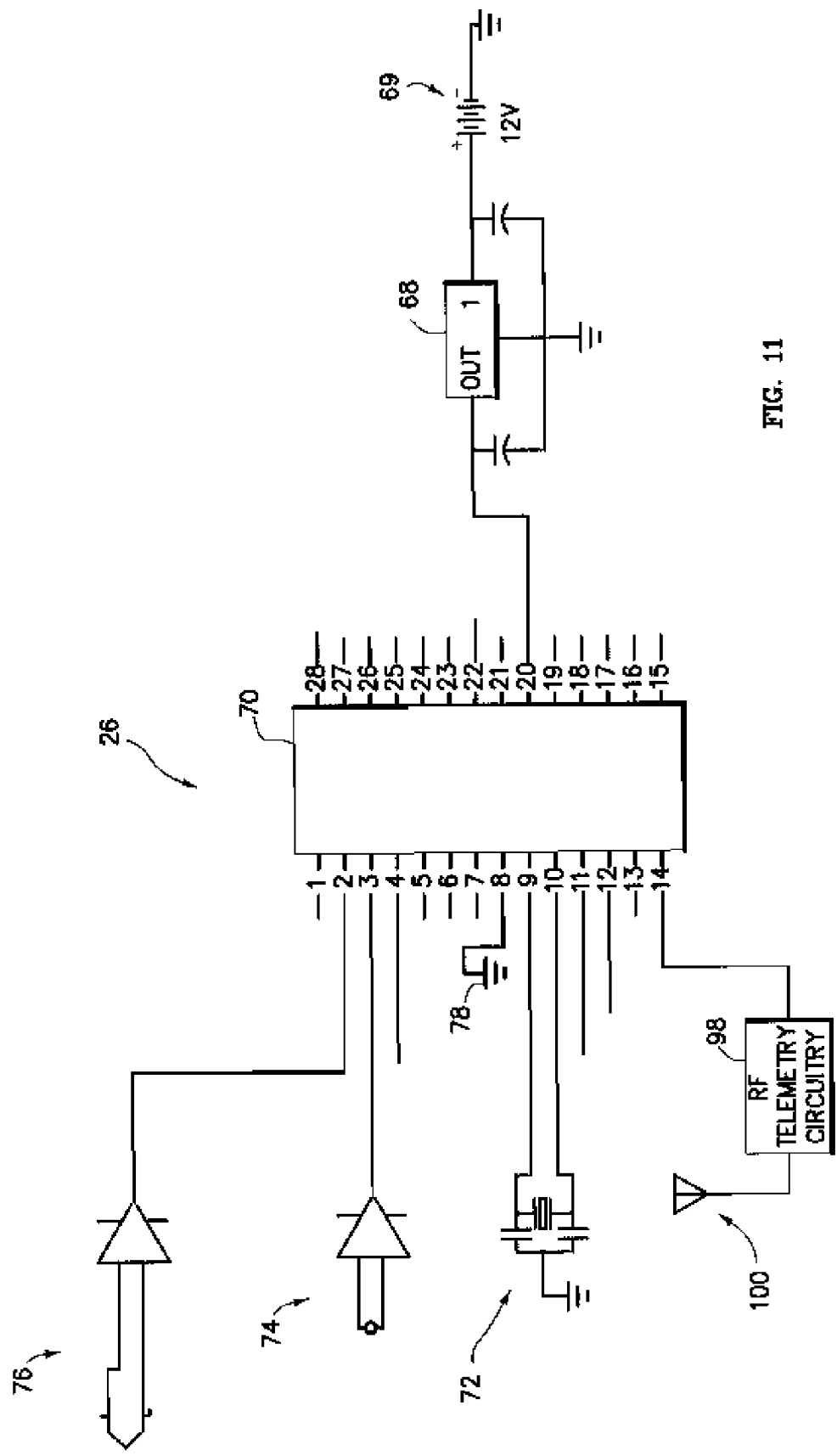
FIG. 11 is an electrical schematic of the general components in the processing receiver.

FIG. 11 is a simplified electrical schematic of the general components in the processing receiver 26. In the center is the microprocessor 70 that processes the information supplied by the thermistor/thermocouple and pH sensor 34 and uses internal instructions to control other devices. The microprocessor 70 has an EEPROM memory section that allows for specific programming to be incorporated as processing instructions. Furthermore, the microprocessor must have the capability to convert analog signals into digital information for decoding and processing. An example of a microprocessor that could be used in the processing receiver 26 is the PIC16F876 28-pin 8-Bin CMOS FLASH micro-controllers manufactured by Microchip Technology, Inc. This particular microprocessor has a 128K EEPROM Data memory bank for flash memory of specific instructions and utilizes a 35-word instruction set. It also has five 10-bit Analog-to-Digital Inputs that are necessary for converting the information obtained from the pH sensor 34 and thermistor 52 from its analog format into a digitized form for processing by the instruction sets of the microprocessor 70.

The microprocessor 70 includes a timing crystal 72 used for clocking operations and is connected to and energized by an approximate 12 volt power supply 69. Also included in the circuit is a nominal 5-volt regulator 68, and a ground 78.

The sensor analog data that is communicated either through direct wiring or through a wireless means that is then amplified by a circuit 74 and connected to the microprocessor 70 through one of the analog-to-digital modules.

In addition, the thermistor analog data that is communicated either through direct wiring or through a wireless means is amplified by circuit 76 and connected to the microprocessor 70 through another one of the analog-to-digital modules.

In certain embodiments, the transmitted data can be recorded, compressed and stored as it is received using a memory chip set or memory circuit within the microprocessor (not shown). Subsequently, the data stored can be downloaded into an external data retrieval device, which can be a computer or other analysis machine.

Figure 12:
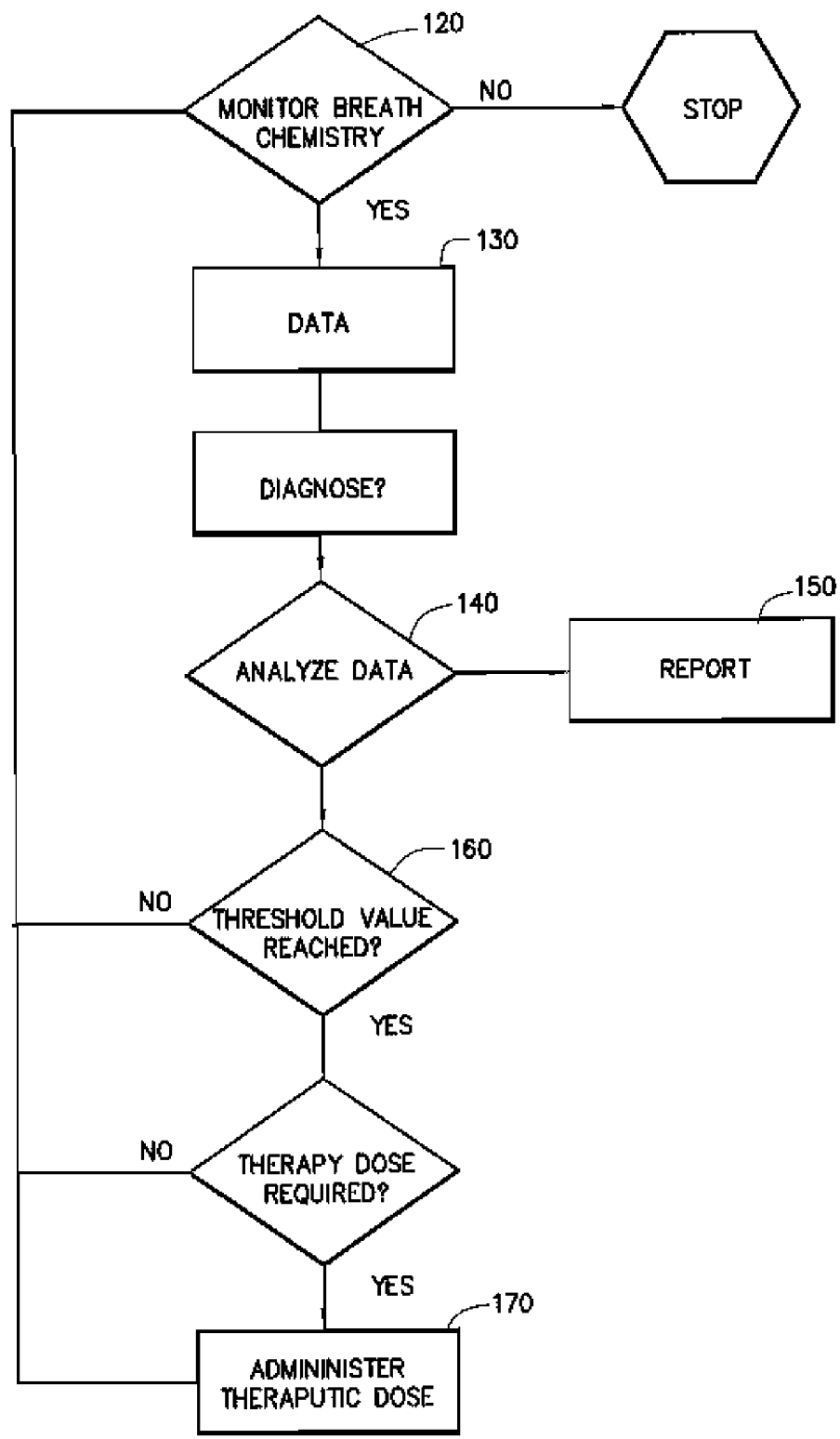
FIGS. 12 and 13 are flowcharts showing the sequential computational steps employed by the processing receiver.
Figure 13:
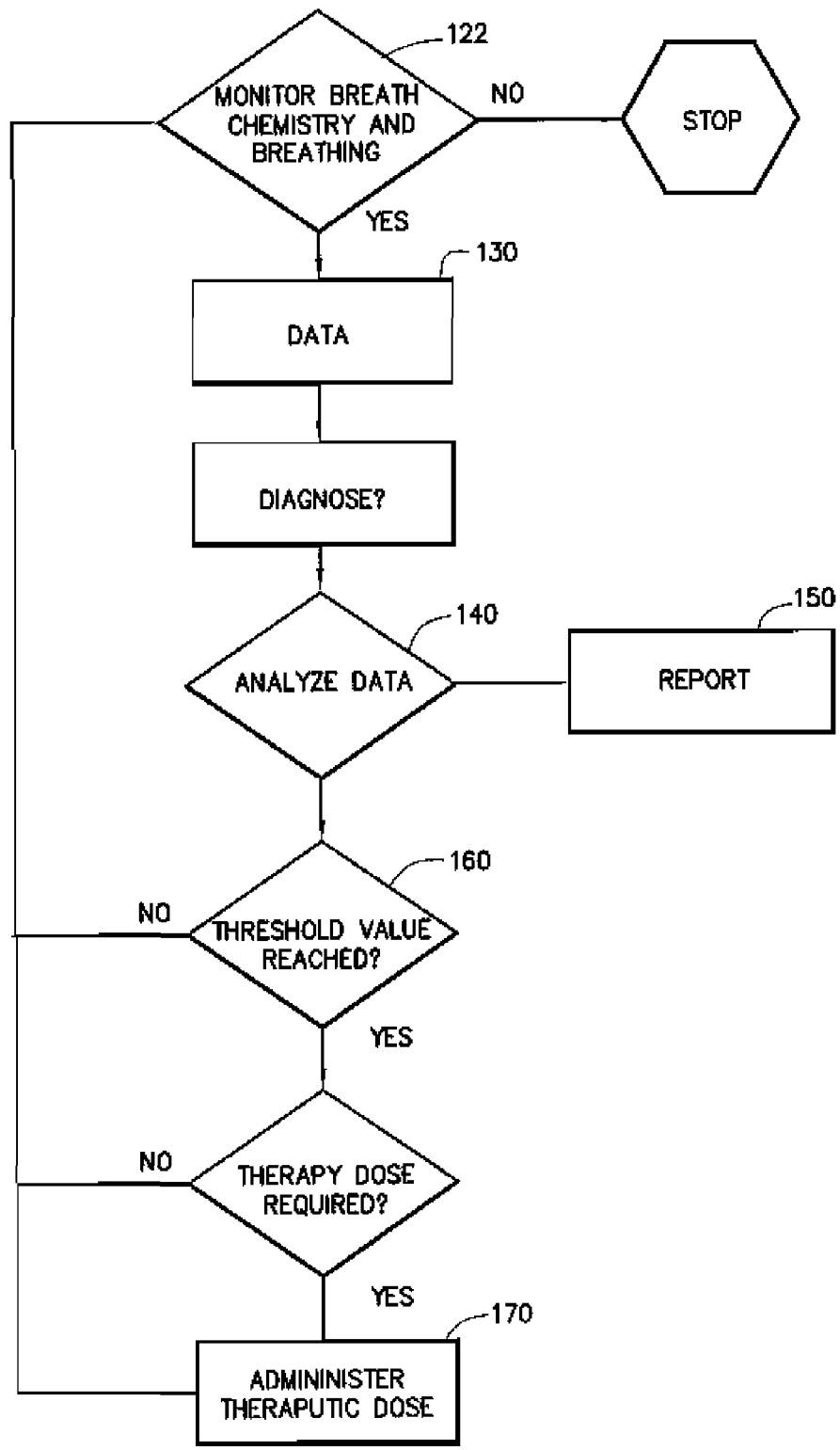

FIGS. 12 and 13 illustrate flowcharts showing the sequential computational steps employed by the processing receiver 26. As described above, the microprocessor 70 has an EEPROM memory section that allows for specific programming to be incorporated as processing instructions. The steps programmed in the microprocessor 70 are outlined in the flowcharts, starting with the 1) monitoring of breath chemistry 120 without CPAP support (FIG. 12) 2) the monitoring of breath chemistry and breathing rates (122) with CPAP support (FIG. 13). The analog information obtained from the sensor and the thermistor is converted to digital information and transferred to the microprocessor. The microprocessor uses the thermistor data to calculate an accurate pH level that is stored in a registry. Optionally, this data can be diagnosed by the microprocessor 140 and stored in a memory bank whereby the microprocessor can create diagnostic reports 150.

The stored data is then compared to a threshold value or range 160 programmed in the instruction set of the microprocessor 70. For example, if the pH level does not reach the threshold value, then no actions are performed and the instruction set loops back to read breath chemistry (FIG. 12) or breath chemistry and monitor breathing rates (FIG. 13). If the pH level reaches the threshold value, then the microprocessor 70 determines the appropriate therapy 170.

It is also anticipated by the Applicants that the present invention diagnostic means will examine the pH waveform patterns produced to diagnose diseases.

These computational steps can be continued over and over again to detect, record, analyze and administer the appropriate therapeutic regime to manage patients with certain respiratory conditions.

The present invention will: 1) Monitor; 2) Diagnose; 3) Treat a respiratory disease, with and without CPAP therapy.

While the invention has been described in detail and with reference to specific embodiments thereof, it will be apparent to one skilled in the art that various changes and modifications can be made therein without departing from the spirit and scope thereof.

We claim:

1. A system for monitoring breath chemistry:
   an apparatus that allows a sample of an individual's breath on a self-condensing sensor;
   said apparatus having a means to replace a sample of condensed breath with a sample of condensed immediately subsequent breath resulting in a continuous real-time self-condensing sensor;
   a processing receiver; and
   said self-condensing sensor providing a continuous real-time communication indicative of said breath chemistry or a medical condition.

2. The system as recited in claim 1, wherein said apparatus is a general mask, nasal cannula, headband with boom apparatus for directing the patient's breath towards said self-condensing sensor.

3. The system as recited in claim 1, wherein said sensor is designed to monitor pH.

4. The system as recited in claim 1, wherein said medical condition is a respiratory condition selected from the group consisting of asthma, laryngopharyngeal reflux disease, chronic obstructive pulmonary disease, sleep apnea.

5. The system as recited in claim 1, wherein said communication is accomplished by a plurality of wires.

6. The system as recited in claim 1, wherein said communication is accomplished by a wireless means.

7. The system as recited in claim 1, wherein said apparatus has a means to replace said sample of condensed breath with a subsequent sample of condensed breath.

8. The system as recited in claim 1, further comprising a coating on a portion of said self-condensing sensor, said coating consisting of hydrophilic polyurethanes, polyacrylamides, poly(2-hydrox-ethyl-methacrylate), other methacrylate copolymers, perfluorinated polymers, polysaccharides, polyvinylchloride polyvinyl alcohol, silicones and any combinations thereof.

9. A system for monitoring breath chemistry and diagnosing a medical condition:
an apparatus that allows a sample of an individual's breath on a self-condensing pH sensor;
a processing receiver;
said self-condensing pH sensor providing a continuous real-time communication indicative of said sample of said individual's breath; and
said processing receiver processing a first information communicated from said sensor for determining various diagnoses.

10. The system as recited in claim 9, wherein said apparatus is a general mask, nasal cannula, headband with boom apparatus, or similar device for directing the patient's breath in close proximity to said self-condensing sensor.

11. The system as recited in claim 9, wherein said medical condition is a respiratory condition selected from the group consisting of asthma, laryngopharyngeal reflux disease, chronic obstructive pulmonary disease, or sleep apnea.

12. The system as recited in claim 9, wherein said communication is accomplished by a plurality of wires.

13. The system as recited in claim 9, wherein said communication is accomplished by a wireless means.

14. The system as recited in claim 9, wherein said apparatus has a means to replace said sample of condensed breath with a subsequent sample of condensed breath.

15. The system as recited in claim 9, further comprising a coating on a portion of said self-condensing sensor, said coating consisting of hydrophilic polyurethanes, polyacrylamides, poly(2-hydrox-ethyl-methacrylate), other methacrylate copolymers, perfluorinated polymers, polysaccharides, polyvinylchloride polyvinyl alcohol, silicones and any combinations thereof.

16. A system for monitoring breath chemistry, diagnosing, and treating a medical condition:
an apparatus that allows a sample of an individual's breath on a self-condensing pH sensor;
a processing receiver;
said self-condensing sensor providing a continuous real-time communication indicative of said sample of said individual's breath;
said processing receiver processing information for determining various diagnoses and treatments; and
said processing receiver in a second communication with at least one treatment device to administer at least one therapeutic dose.

17. The system as recited in claim 16, wherein said apparatus is a general mask, nasal cannula, headband with boom apparatus, or similar device for directing the patient's breath in close proximity to said self-condensing sensor.

18. The system as recited in claim 16, wherein said medical condition is a respiratory condition selected from the group consisting of asthma, laryngopharyngeal ref lux disease, chronic obstructive pulmonary disease, or sleep apnea.

19. The system as recited in claim 16, wherein said first communication is accomplished by a plurality of wires.

20. The system as recited in claim 16, wherein said first communication is accomplished by a wireless means.

21. The system as recited in claim 16, wherein said second communication is accomplished by a plurality of wires.

22. The system as recited in claim 16, wherein said second communication is accomplished by a wireless means.

23. The system as recited in claim 16, wherein said treatment is a biocompatible agent capable of neutralizing an acidic condition.

24. The system as recited in claim 16, wherein said treatment is sodium bicarbonate.

25. The system as recited in claim 16, further comprising a communication between said processing receiver and a nebulizer, an atomizer, and/or a humidifier.

26. The system as recited in claim 16, further comprising a third communication between said processing receiver and a continuous positive airway pressure device.

27. A system for monitoring breath chemistry:
an apparatus that directs a sample of an individual's breath on a self-condensing sensor assembly for monitoring pH;
said self-condensing sensor assembly for monitoring pH consisting of an outer tubular member and an inner tubular member, said outer tubular member enclosing an inner tubular member, an antimony sensor enclosed within said inner tubular member, a reference element enclosed within said outer tubular member and located in a proximal position, a wick material, said wick material having one side which partially surrounds and substantially engages a portion of said inner tubular member, said wick material extending from said antimony sensor to a proximal position whereby said wick material is substantially engaged to said reference element, and an ion conduction media entrained or retained within said wick material;
a processing receiver; and
said self-condensing sensor providing a continuous real-time communication indicative of said breath pH level.

28. The system as recited in claim 27, further comprising said processing receiver analyzing breath pH level information for determining various diagnoses.

29. The system as recited in claim 27, wherein said wick material is selected from the group consisting of fibrous polymeric meshes of polyester, polyimide, polyethylene, polypropylene, polyvinyl chloride, polystyrene, ABS, nylon, delrin, or polyethylene terephthalate (PET), polytetrafluoroethylene (PTFE), polysaccharide, or any combinations thereof.

30. The system as recited in claim 27, wherein said wick is a porous material selected from the group consisting of porous ceramic, metallic or polymeric materials.

31. The system as recited in claim 27, wherein said ion conduction media contains a polysaccharide based material.

32. The system as recited in claim 27, wherein said ion conduction media comprises an electrolyte/water based gel.

33. The system as recited in claim 27, wherein said ion conduction media comprises a conductive polymer.

34. The system as recited in claim 27, wherein said reference element comprises silver chloride.

35. The system as recited in claim 27, wherein said reference element comprises a silver element having a silver chloride coating.

36. The system as recited in claim 27, further comprising an electrical and display means which is in communication with the sensor and processes information obtained from said sensor for presenting a pH reading.

37. The system as recited in claim 27, wherein said apparatus is a general mask, nasal cannula, headband with boom apparatus, or similar device for directing the patient's breath in close proximity to said self-condensing sensor.

38. The system as recited in claim 27, wherein said medical condition is a respiratory condition selected from the group consisting of asthma, laryngopharyngeal reflux disease, chronic obstructive pulmonary disease, or sleep apnea.

39. The system as recited in claim 27, wherein said first communication is accomplished by a plurality of wires.

40. The system as recited in claim 27, wherein said first communication is accomplished by a wireless means.

41. The system as recited in claim 27, further comprising a coating on a portion of said self-condensing sensor, said coating consisting of hydrophilic polyurethanes, polyacrylamides, poly (2-hydrox-ethyl-methacrylate), other methacrylate copolymers, perfluorinated polymers, polysaccharides, polyvinylchloride polyvinyl alcohol, silicones and any combinations thereof.

42. A system as recited in claim 27, wherein said outer tubular member coaxially encloses said inner tubular member.

43. A system as recited in claim 27, wherein said outer tubular member co-linearly encloses said inner tubular member.

44. The system as recited in claim 43, wherein said co-linear configuration between said outer tubular member and said inner tubular member are offset.

45. A system for monitoring breath chemistry:
an apparatus that directs a sample of an individual's breath on a self-condensing sensor assembly for monitoring pH;
said self-condensing sensor assembly for monitoring pH consisting of an outer tubular member and an inner tubular member, said outer tubular member enclosing an inner tubular member, an antimony sensor enclosed within said inner tubular member, a reference element enclosed within said outer tubular member and located in a proximal position, a wick material, said wick material having one side which partially surrounds and substantially engages a portion of said inner tubular member, said wick material extending from said antimony sensor to a proximal position whereby said wick material is substantially engaged to said reference element, and an ion conduction media entrained or retained within said wick material;
a processing receiver;
said self-condensing sensor providing a continuous real-time communication indicative of said breath chemistry;
said processing receiver analyzing said breath chemistry information for determining various diagnoses and treatments; and
said processing receiver in a treatment communication with at least one treatment device to administer at least one therapeutic dose for a medical condition.

46. The system as recited in claim 45, wherein said wick material is selected from the group consisting of fibrous polymeric meshes of polyester, polyimide, polyethylene, polypropylene, polyvinyl chloride, polystyrene, ABS, nylon, delrin, or polyethylene terephthalate (PET), polytetrafluoroethylene (PTFE), polysaccharide, or any combinations thereof.

47. The system as recited in claim 45, wherein said wick is a porous material selected from the group consisting of porous ceramic, metallic or polymeric materials.

48. The system as recited in claim 45, wherein said ion conduction media contains a polysaccharide based material.

49. The system as recited in claim 45, wherein said ion conduction media comprises an electrolyte/water based gel.

50. The system as recited in claim 45, wherein said ion conduction media comprises a conductive polymer.

51. The system as recited in claim 45, wherein said reference element comprises silver chloride.

52. The system as recited in claim 45, wherein said reference element comprises a silver element having a silver chloride coating.

53. The system as recited in claim 45, further comprising an electrical and display means which is in communication with the sensor and processes information obtained from said sensor for presenting a pH reading.

54. The system as recited in claim 45, wherein said apparatus is a general mask, nasal cannula, headband with boom apparatus, or similar device for directing the patient's breath in close proximity to said self-condensing sensor.

55. The system as recited in claim 45, wherein said medical condition is a respiratory condition selected from the group consisted of asthma, laryngopharyngeal reflux disease, chronic obstructive pulmonary disease, or sleep apnea.

56. The system as recited in claim 45, wherein said real-time communication is accomplished by a plurality of wires.

57. The system as recited in claim 45, wherein said real-time communication is accomplished by a wireless means.

58. The system as recited in claim 45, wherein said treatment communication is accomplished by a plurality of wires.

59. The system as recited in claim 45, wherein said treatment communication is accomplished by a wireless means.

60. The system as recited in claim 45, wherein said treatment is a biocompatible agent capable of neutralizing an acidic condition.

61. The system as recited in claim 45, wherein said treatment is sodium bicarbonate.

62. The system as recited in claim 45, further comprising a communication between said processing receiver and a nebulizer/atomizer/humidifier.

63. The system as recited in claim 45, further comprising a third communication between said processing receiver and a continuous positive airway pressure device.

64. The system as recited in claim 45, further comprising a coating on a portion of said self-condensing sensor, said coating consisting of hydrophilic polyurethanes, polyacrylamides, poly(2-hydrox-ethyl-methacrylate), other methacrylate copolymers, perfluorinated polymers, polysaccharides, polyvinylchloride polyvinyl alcohol, silicones and any combinations thereof.

65. A system as recited in claim 45, wherein said outer tubular member coaxially encloses said inner tubular member.

66. A system as recited in claim 45, wherein said outer tubular member co-linearly encloses said inner tubular member.

67. The system as recited in claim 66, wherein said co-linear configuration between said outer tubular member and said inner tubular member are offset.

\* \* \* \* \*